US012751655B2

(12) United States Patent
Ahlberg et al.

(10) Patent No.: US 12,751,655 B2
(45) Date of Patent: Oct. 6, 2026

(54) ACTIVATION AND RETRACTION MECHANISM FOR LANCING DEVICES

(71) Applicant: Safety Lancet Sweden AB, Gothenburg (SE)

(72) Inventors: Björn Ahlberg, Stockholm (SE); John Hamberg, Värmdö (SE); Ingvar Sjöqvist, Älvsjö (SE)

(73) Assignee: SAFETY LANCET SWEDEN AB, Gothenburg (SE)

( * ) Notice: Subject to any disclaimer, the term of this patent is extended or adjusted under 35 U.S.C. 154(b) by 943 days.

(21) Appl. No.: 17/206,844

(22) Filed: Mar. 19, 2021

(65) Prior Publication Data

US 2021/0204848 A1 Jul. 8, 2021

Related U.S. Application Data

(63) Continuation of application No. PCT/SE2019/050826, filed on Sep. 4, 2019.

(30) Foreign Application Priority Data

Sep. 20, 2018 (SE) .................................... 1851116-2

(51) Int. Cl.
*A61B 5/151* (2006.01)
*A61B 5/15* (2006.01)

(52) U.S. Cl.
CPC ...... *A61B 5/1519* (2013.01); *A61B 5/150022* (2013.01); *A61B 5/150549* (2013.01); *A61B 5/15117* (2013.01); *A61B 2560/04* (2013.01)

(58) Field of Classification Search
CPC ............ A61B 5/1519; A61B 5/150022; A61B 5/150549; A61B 5/15117;
(Continued)

(56) References Cited

U.S. PATENT DOCUMENTS 4,892,097 A * 1/1990 Ranalletta ........ A61B 5/150259 606/182
4,924,879 A 5/1990 O'Brien
(Continued)

FOREIGN PATENT DOCUMENTS

CN 201098127 Y * 8/2008 ........... A61B 5/1411
CN 106491142 A 3/2017
(Continued)

OTHER PUBLICATIONS

CN-201098127-Y English Translation (Year: 2008).*

*Primary Examiner* — Aurelie H Tu
*Assistant Examiner* — Andrew E Hoffpauir
(74) *Attorney, Agent, or Firm* — Ballard Spahr LLP

(57) ABSTRACT

Described is an activation/retraction mechanism for a lancing device that has a pusher that includes a first biasing member arranged to displace the pusher in a distal direction; and a lancet holder that includes a lancet for penetrating the skin of a subject, and a second biasing member arranged to displace the lancet holder in a proximal direction. The lancet holder and the pusher are arranged in a housing so that a distal end of the pusher engages a proximal end of the lancet holder to push the lancet holder in a distal direction when the first biasing member displaces the pusher distally. The distal end of the pusher and the proximal end of the lancet holder are arranged to disengage from each other when the pusher has been displaced distally a predetermined length from its initial position.

18 Claims, 7 Drawing Sheets

(58) Field of Classification Search
CPC .......... A61B 5/150908; A61B 5/15113; A61B 5/15144; A61B 5/150412; A61B 5/15194; A61B 5/150106; A61B 5/151; A61B 2560/04
See application file for complete search history.

(56) References Cited

U.S. PATENT DOCUMENTS

| | | | | |
|---|---|---|---|---|
| 6,036,924 | A * | 3/2000 | Simons | A61B 5/15113 600/583 |
| 6,231,531 | B1 | 5/2001 | Lum et al. | |
| 6,830,551 | B1 * | 12/2004 | Uchigaki | A61B 5/150022 600/347 |
| 8,709,033 | B2 * | 4/2014 | Kim | A61B 5/150022 606/182 |
| 2005/0145520 | A1 * | 7/2005 | Ilo | A61B 5/150183 206/365 |
| 2006/0020228 | A1 * | 1/2006 | Fowler | A61B 5/150022 600/583 |
| 2007/0185515 | A1 * | 8/2007 | Stout | A61B 5/15144 606/181 |
| 2007/0293882 | A1 * | 12/2007 | Harttig | A61B 5/150519 606/181 |
| 2009/0036915 | A1 * | 2/2009 | Karbowniczek | A61B 5/1513 606/182 |
| 2009/0264911 | A1 | 10/2009 | Kim | |
| 2009/0270765 | A1 * | 10/2009 | Ghesquiere | C12Q 1/54 600/583 |
| 2009/0275969 | A1 * | 11/2009 | Kitamura | A61B 5/1513 606/181 |
| 2011/0029006 | A1 * | 2/2011 | Leong | A61B 5/150893 606/182 |
| 2011/0144537 | A1 * | 6/2011 | Robbins | A61B 5/150717 600/583 |
| 2013/0085517 | A1 * | 4/2013 | Keil | A61B 5/150519 606/182 |
| 2013/0123824 | A1 * | 5/2013 | Vine | A61B 5/150435 606/181 |
| 2013/0338537 | A1 * | 12/2013 | Pusey | A61B 5/15117 600/583 |
| 2014/0088633 | A1 * | 3/2014 | Kan | A61B 5/150152 606/182 |
| 2014/0206969 | A1 * | 7/2014 | Lee | A61B 5/1411 600/365 |
| 2015/0005668 | A1 * | 1/2015 | Richter | A61B 5/150435 600/583 |
| 2016/0317072 | A1 * | 11/2016 | Calvert | A61B 5/15111 |
| 2017/0000517 | A1 * | 1/2017 | Lee | A61B 5/1519 |

FOREIGN PATENT DOCUMENTS

| | | | | |
|---|---|---|---|---|
| CN | 106580340 | A | 4/2017 | |
| CN | 107334479 | A | 11/2017 | |
| CN | 107951494 | A | 4/2018 | |
| EP | 1247489 | A1 | 10/2002 | |
| WO | WO-2008140464 | A2 * | 11/2008 | A61B 5/15176 |
| WO | 2009052710 | A1 | 4/2009 | |
| WO | 2009129349 | A2 | 10/2009 | |
| WO | WO-2011158669 | A1 * | 12/2011 | A61B 5/15144 |
| WO | 2018022535 | A1 | 2/2018 | |

* cited by examiner

ACTIVATION AND RETRACTION MECHANISM FOR LANCING DEVICES

This application is the continuation of international Application No. PCT/SE2019/050826, filed 4 Sep. 2019, which claims the benefit of Swedish patent application SE 1851116-2, filed 20 Sep. 2018, the entire contents of which are hereby incorporated by reference.

TECHNICAL FIELD

The present invention relates generally to lancing devices, more specifically to an improved activation/retraction mechanism for lancing devices and a lancing device comprising such a mechanism.

BACKGROUND ART

Lancing devices are used to penetrate the skin of a subject and obtain a sample of blood or other body fluid, e.g. in the testing of blood sugar levels by diabetics. Typically, a lancet having a sharp point is translationally mounted within a housing portion of a lancing device. The lancet is driven by a spring or other biasing means to cause the sharp point to extend a small distance through an opening in the housing and into the subject's skin, creating a wound from which the sample of body fluid is collected.

Lancing devices typically are intended either for single-use or for multiple uses. Single-use lancing devices generally are disposed of after one use. For example, in a hospital or clinic, it is desirable to provide a single-use lancing device that can be used on a patient and then disposed of to eliminate any risk of infection to subsequent patients or caregivers from exposure to residual body fluids remaining on the lancing device. Accordingly, single-use lancing devices oftentimes include a disabling mechanism to prevent accidental or unintentional re-use of the device. Various forms of disabling mechanisms are available and are well known in the art. For example, the disabling mechanism may comprise a return spring for retracting the sharp point of the lancet back into the housing after use, as well as break-away elements or a frangible link in the cocking or triggering mechanism to prevent re-arming or re-firing the device after use, a locking element, and/or a shield for blocking travel of the lancet.

One problem experienced by many subjects is that the sharp point of the lancet causes significant pain during penetration. Many lancing devices seek to ease the pain by allowing for adjustment of the penetration depth of the lancet. On the other hand, in order to obtain a sufficient size for a blood sample, the penetration depth should be sufficient to penetrate the epidermis and puncture a capillary.

Another issue affecting the level of pain experienced by the subject is the actual time that the sharp point of the lancet remains in the subject's skin. In lancing devices employing a retraction mechanism including a return spring, the spring force of the activation spring is many times greater than that of the return spring to achieve a sufficiently rapid and powerful lancing stroke. Hence, the sharp point of the lancet remains a considerable period of time in the subject's skin before the return spring is able to overcome the spring force of the activation spring. Examples of such lancing devices are given in U.S. 2013/0123824, U.S. 2007/0185515, and U.S. 2007/0293882.

Thus, there is a need for a solution which reduces the time that the sharp point of the lancet remains in the subject's skin.

SUMMARY OF THE INVENTION

An object of the present invention is to provide an improved activation/retraction mechanism for a lancing device which rapidly returns the lancet into the housing after penetration into the subject's skin. This object is achieved in a first aspect of the invention, in which there is provided an activation/retraction mechanism for a lancing device comprising: a pusher comprising a first biasing member arranged to displace the pusher in a distal direction; and a lancet holder comprising a lancet for penetrating the skin of a subject and a second biasing member arranged to displace the lancet holder in a proximal direction; wherein the lancet holder and the pusher are arranged in a housing of the lancing device in such a way that a distal end of the pusher engages a proximal end of the lancet holder to push the lancet holder in a distal direction when the first biasing member displaces the pusher distally, wherein the distal end of the pusher and the proximal end of the lancet holder are arranged to disengage from each other when the pusher has been displaced distally a predetermined length from its initial position, i.e. the length of the firing/lancing stroke, whereby the lancet holder may return to its initial position under influence of the second biasing member.

By providing means for disengaging the pusher and the lancet holder at the end of the firing stroke, the lancet holder may be retracted more rapidly into the housing without needing to overcome the force of the biasing member, thus reducing the time that the lancet remains in the skin.

In preferred embodiment, a distal portion of the pusher and the proximal portion of the lancet holder have complementary cross-sections and have a combined cross-sectional area smaller than the cross-sectional area of the housing such that the distal portion of the pusher and the proximal portion of the lancet holder are free to move in relation to each other when the distal end of the pusher is disengaged from the proximal end of the lancet holder. Preferably, the cross-sectional area of each of the distal portion of the pusher and the proximal portion of the lancet holder is approximately half of the cross-sectional area of the housing to allow the proximal portion of the lancet holder to pass by the distal portion of the pusher and return to its initial position.

In an advantageous embodiment, the pusher and the lancet holder are arranged at a non-zero angle to each other such that the distal end of the pusher moves laterally in relation to the proximal end of the lancet holder when the first biasing member displaces the pusher distally until they disengage from each other.

In an alternative embodiment, the pusher comprises an external helical groove or ridge arranged to cooperate with a guide projection arranged in the housing to rotate the pusher when the first biasing member displaces the pusher distally, such that the distal end of the pusher rotates in relation to the proximal end of the lancet holder until they disengage from each other.

The above embodiments present different alternatives for displacing the pusher and the lancet holder in relation to each other (lateral movement enabled by the non-zero angle or rotational movement), separate from the firing/lancing displacement in the distal direction, in order to disengage the proximal end of the lancet holder from the distal end of the pusher.

In a further preferred embodiment, the pusher comprises at least one pusher arm extending in a distal direction, wherein a distal end of the at least one pusher arm comprises an engagement surface arranged to engage the proximal end of the lancet holder and a camming surface, wherein the camming surface is arranged to come into contact with an abutment in the housing arranged in a position corresponding to the predetermined length from the initial position of the pusher, and adapted to deflect the at least one pusher arm laterally to disengage the at least one pusher arm from the proximal end of the lancet holder when the pusher is urged against the abutment in the distal direction. Preferably, the pusher comprises two pusher arms. The provision of pusher arm(s) reduces the bulk of the pusher as well as enables using deflection to disengage the pusher arm(s) from the proximal end of the lancet holder.

In an advantageous embodiment, the activation/retraction mechanism further comprises a safety assembly comprising a lancet guard integrally formed with a distal end of the lancet holder by means of a frangible portion adapted to break when the lancet guard is displaced in relation to the lancet holder, e.g. by a twisting and/or pulling motion. The lancet guard provides additional protection against accidental puncture from the exposed sharp point of the lancet. The frangible portions facilitate removal of the lancet guard.

In a preferred embodiment, the lancet holder further comprises one or more projections arranged to cooperate with corresponding recesses in the housing which allow rotation of the lancet holder within a predetermined angular range. The projections allow the lancet holder to be rotated (e.g. by twisting the lancet guard) a predetermined angle and then prevents further rotation. Thus, continued twisting of the lancet guard will break the frangible portions to allow removal of the lancet guard. It is understood that the solution incorporating the lancet guard and twisting for removal may be employed independently in a lancing device, separate from the function of disengaging the pusher from the lancet holder.

In a further preferred embodiment, the safety assembly further comprises a guide rod rigidly connected to or integrally formed with a proximal end of the lancet holder, wherein the pusher comprises a through-going hole adapted to the shape of the guide rod such that rotation of the lancet holder a predetermined angle in relation to the pusher brings the guide rod into alignment with the hole to allow the pusher to be displaced distally along the guide rod. The guide rod provides additional safety in that it prevents accidental firing of the lancing device. It is understood that the solution incorporating the guide rod and cooperating hole in the pusher for preventing accidental firing may be employed independently in a lancing device, separate from the function of disengaging the pusher from the lancet holder.

In an advantageous embodiment, the first and/or second biasing member comprises a resilient spring. A resilient spring may have different characteristics (spring force, length, etc.) adapted to the desired specification of the lancing device.

In an alternative embodiment, the first biasing member comprises a spiral wound torsion spring arranged in a proximal end of the housing with its axis of rotation substantially perpendicular to the longitudinal extension of the housing, wherein a free end of the torsion spring extends a predetermined length from the axis of rotation and is arranged to act as the pusher, wherein rotation of the torsion spring causes the free end to engage the proximal end of the lancet holder and displace the lancet holder distally, wherein the housing comprises a recess arranged to receive the free end of the torsion spring when the free end reaches its distalmost position in such a way that the free end is disengaged from the proximal end of the lancet holder. This alternative embodiment combines the pusher and the first biasing member in one component, further simplifying the construction of the lancing device to facilitate manufacture and reduce costs.

In an advantageous embodiment, the activation/retraction mechanism further comprises a releasable locking member arranged to retain the pusher and the first biasing member in a prestressed state. The locking member is activated to release the pusher, i.e. launching the firing stroke of the lancing device.

In a further preferred embodiment, the pusher is arranged at a distance from the lancet holder in an initial stage such that the distal end of the pusher is separated from the proximal end of the lancet holder. By letting the pusher travel an initial distance before engaging the lancet holder, a ‘hammer’ effect is achieved wherein the distal end of the pusher strikes the proximal end of the lancet holder to propel it rapidly in a distal direction, overwhelming the second biasing member. The hammer effect thus increases the speed of the lancing stroke.

In a second aspect of the present invention, there is provided a lancing device comprising an activation/retraction mechanism according to the first aspect.

BRIEF DESCRIPTION OF DRAWINGS

The invention is now described, by way of example, with reference to the accompanying drawings, in which.

DETAILED DESCRIPTION OF EMBODIMENTS

Figures 1A, 1B, 1C, 1D:
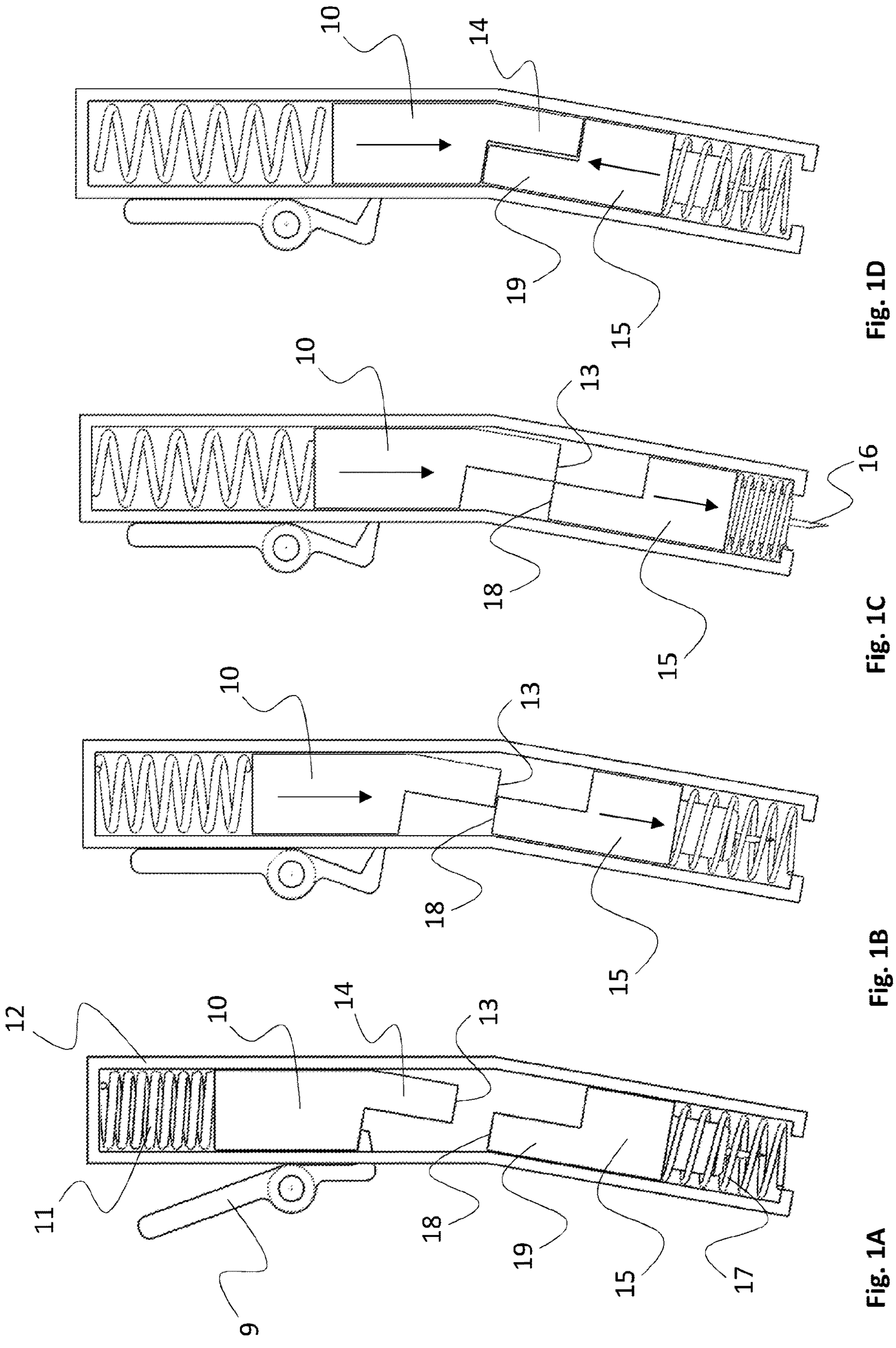
FIGS. 1A-1D show cross-sectional views of an activation/retraction mechanism according to a first embodiment of the present invention in different stages of operation.

In the following, a detailed description of an activation/retraction mechanism for a lancing device according to the invention is presented. In the drawing figures, like reference numerals designate identical or corresponding elements throughout the several figures. It will be appreciated that these figures are for illustration only and are not in any way restricting the scope of the invention.

It is understood that in the context of the present invention, the term ‘distal’ shall be interpreted as referring to a direction away from or portion furthest from the operator handling the lancing device. Likewise, the term ‘proximal’ shall be interpreted as referring to a direction towards or closest to the operator handling the lancing device. In cases where the operator is the same as the subject, e.g. diabetes patients using the lancing device on themselves, the terms shall be interpreted from the perspective of the operator, regardless of the subject.

As explained above, the present invention aims at minimising the pain experienced by a subject when penetrating the skin using a lancing device to obtain a blood sample. The overall concept common to all embodiments described below is that the component (pusher) urging the lancet forward is decoupled from the component (holder) holding the lancet at the end of the firing stroke to allow a more rapid retraction of the lancet from the skin.

FIGS. 1A-1D show a first embodiment of an activation/retraction mechanism for a lancing device according to the present invention during different stages of operation. Generally, the activation/retraction mechanism comprises a pusher 10 adapted to be displaced distally by means of a first biasing member 11 and a lancet holder 15 comprising a lancet 16 and adapted to be engaged and displaced distally by the pusher 10. Further, the lancet holder 15 is arranged to be displaced in a proximal direction by a second biasing member 17. The pusher 10 including the first biasing member 11, and the lancet holder 15 including the lancet 16 and the second biasing member 17 are arranged in a housing. FIGS. 1A-1D show the internal space of the housing and the components arranged therein.

FIG. 1A shows the activation/retraction mechanism in an initial stage (before firing) wherein the pusher 10 is retained in a proximal position by a releasable locking member 9. The first biasing member 11 is here compressed in a prestressed state. The locking member 9 is here shown as a lever with a catch engaging the pusher 10 and is arranged to pivot about an axis to release the pusher 10. Other variants of the locking member 9 are also envisaged.

The lancet holder 15 is arranged in a distal portion 14 of the housing and comprises a lancet 16 at a distal end 13 thereof. The lancet holder 15 is biased proximally towards a retracted position, in which the lancet 16 is accommodated in the housing without protruding therefrom, by means of a second biasing member 17. The second biasing member 17 is here in a relaxed state.

As may be seen, the distal portion 14 of the housing, wherein the lancet holder 15 is arranged, is angled with respect to the proximal portion 19 of the housing, wherein the pusher 10 is arranged. Furthermore, the distal portion 14 of the pusher 10 is oriented at an angle to the longitudinal extension of the pusher 10, which angle substantially corresponds to the angle of the distal portion 14 of the housing with respect to the proximal portion 19. Moreover, the shape and/or cross-section of the distal portion 14 of the pusher 10 corresponds to the shape and/or cross-section of the proximal portion 19 of the lancet holder 15. For instance, both the pusher 10 and the lancet holder 15 may have generally cylindrical shapes, whereas the distal portion 14 of the pusher 10 and the proximal portion 19 of the lancet holder 15 may both have the shape of a half-cylinder. Other complementary shapes are also contemplated which fulfil the criteria that the distal portion 14 of the pusher 10 and the proximal portion 19 of the lancet holder 15 are free to move in relation to each other in a distal and proximal direction, respectively, at the end of the firing stroke of the pusher 10, i.e. when the proximal end 18 of the lancet holder 15 is disengaged from the distal end 13 of the pusher 10.

In FIG. 1B, the locking member 9 has been actuated and the pusher 10 has been released to move in a distal direction under influence of the first biasing member 11. After travelling a short distance, the distal end 13 of the pusher 10 reaches and abuts against the proximal end 18 of the lancet holder 15. Further displacement of the pusher 10 thus also displaces the lancet holder 15 in a distal direction. By letting the pusher 10 travel an initial distance before engaging the lancet holder 15, a 'hammer' effect is achieved wherein the distal end 13 of the pusher 10 strikes the proximal end 18 of the lancet holder 15 to propel it rapidly in a distal direction, overwhelming the second biasing member 17. Of course, the pusher 10 and the lancet holder 15 may be arranged such that the distal end 13 of the pusher 10 engages the proximal end 18 of the lancet holder 15 already in the initial state of the activation/retraction mechanism.

In FIG. 1C, at or near the end of the firing stroke, the pusher 10 has almost reached its distalmost position. The lancet holder 15 has also reached its distalmost position wherein the lancet 16 extends out of the distal opening of the housing to penetrate the skin, and the second biasing member 17 has been compressed. As may be seen in FIG. 1C, the pusher 10 has been displaced distally, but the distal portion 14 of the pusher 10 has also been displaced laterally in relation to the proximal portion 19 of the lancet holder 15. Simultaneously with the distal displacement, the distal end 13 of the pusher 10 slides laterally with respect to the proximal end 18 of the lancet holder 15 until their respective end surfaces lose contact with each other, and as a result, the proximal end 18 of the lancet holder 15 is disengaged from the distal end 13 of the pusher 10.

FIG. 1D shows the activation/retraction mechanism in a final stage, wherein the pusher 10 has been displaced to its distalmost position. Due to the complementary shapes of the distal portion 14 of the pusher 10 and the proximal portion 19 of the lancet holder 15, the lancet holder 15 is allowed to be displaced by the second biasing member 17 in a proximal direction towards its initial, retracted position, wherein the lancet 16 does not protrude from the housing. Each of the distal portion 14 of the pusher 10 and the proximal portion 19 of the lancet holder 15, respectively, comprises a recess adapted to accommodate the corresponding protruding portion of the other component.

Turning now to FIGS. 2A-2E, an alternative embodiment of the activation/retraction mechanism working under a similar principle to the one shown in FIGS. 1A-1D is illustrated. This alternative activation/retraction mechanism provides relative movement of the pusher 20 and the lancet holder 25, separate from the distal displacement. In FIGS. 2A-2E, the housing, the locking member, and the biasing members acting on the components have been omitted so as not to clutter the drawings. However, it should be understood that said components are present in conjunction with the activation/retraction mechanism as a whole.

Figures 2A, 2B, 2C, 2D, 2E:
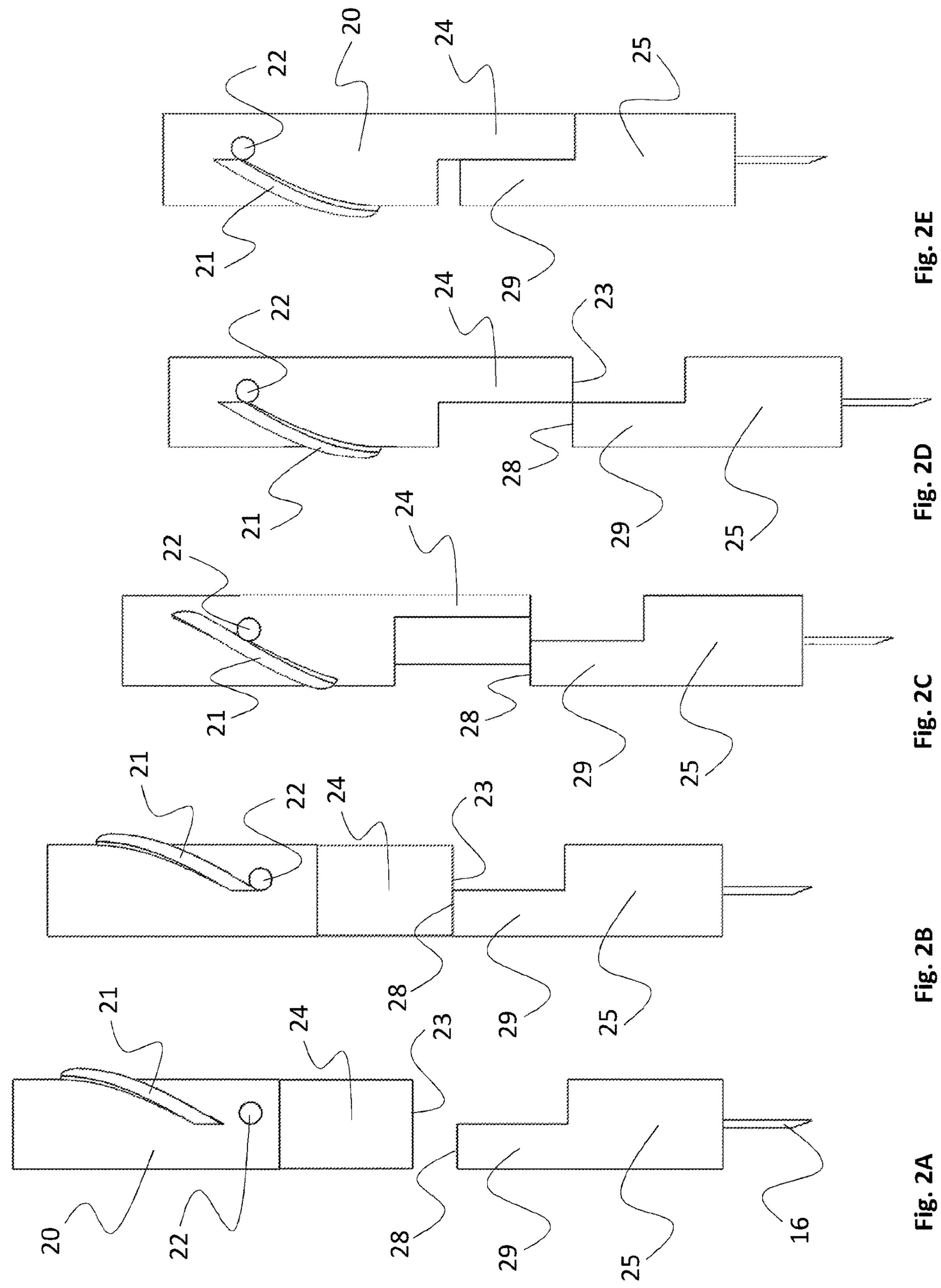
FIGS. 2A-2E show views of an activation/retraction mechanism according to a second embodiment of the present invention in different stages of operation.

FIG. 2A shows the activation/retraction mechanism in an initial stage (before firing) wherein the pusher 20 is retained in a proximal position, and the lancet holder 25 is biased towards its proximal position with the lancet not protruding from the housing. The pusher 20 comprises a helical ridge 21 or guide groove 21 extending along part of its circumferential surface. The ridge 21 is arranged to cooperate with a projection 22 arranged on the internal surface of the housing, as will be further explained below.

FIG. 2B shows the activation/retraction mechanism shortly after firing, the pusher 20 has been released and displaced distally by the first biasing member so that the distal end 23 of the pusher 20 abuts against the proximal end 28 of the lancet holder 25. Simultaneously, the ridge 21 has been brought into engagement with the projection 22 on the housing.

FIG. 2C shows the activation/retraction mechanism in a further advanced stage, wherein the pusher 20 and the lancet holder 25 both have been displaced further in a distal direction owing to the abutment between the distal end 23 of the pusher 20 and the proximal end 28 of the lancet holder 25. At the same time, the helical path of the ridge 21 slides against the projection 22 to cause the pusher 20 to rotate in relation to the housing and the lancet holder 25. As a result, the area of contact between the distal end 23 of the pusher 20 and the proximal end 28 of the lancet holder 25 decreases.

FIG. 2D shows the activation/retraction mechanism at or near the end of the firing stroke. The pusher 20 has reached its distalmost position and has also been rotated a quarter-turn, approximately 90° about the longitudinal axis of the pusher 20. The lancet holder 25 has also reached its distalmost position, wherein the lancet extends out of the distal opening of the housing to penetrate the skin. At this point, the area of contact between the distal end 23 of the pusher 20 and the proximal end 28 of the lancet holder 25 reaches its minimum and becomes zero, in other words, the proximal end 28 of the lancet holder 25 is disengaged from the distal end 23 of the pusher 20.

FIG. 2E shows the activation/retraction mechanism in a final stage. Due to the complementary shapes of the distal portion 24 of the pusher 20 and the proximal portion 29 of the lancet holder 25, the lancet holder 25 is allowed to be displaced by the second biasing member in a proximal direction towards its initial, retracted position, wherein the lancet does not protrude from the housing. Each of the distal portion 24 of the pusher 20 and the proximal portion 29 of the lancet holder 25, respectively, comprises one or more recesses adapted to accommodate the corresponding protruding portions of the other component. For instance, the distal portion 24 of the pusher 20 may comprise one or more protruding members and the proximal portion 29 of the lancet holder 25 may comprise correspondingly shaped recesses, or vice versa. As the pusher 20 is rotated by the action of the projection 22 and the helical ridge 21, the protruding members are brought into alignment with the recesses. When aligned, the protruding members will be received in the recesses as the lancet holder 25 is displaced in the proximal direction.

Similar to the embodiment described with reference to FIGS. 1A-1D, the shape and/or cross-section of the distal portion 24 of the pusher 20 and the proximal portion 29 of the lancet holder 25 are adapted to correspond to each other in such a way to allow free movement of the lancet holder 25 in a proximal direction in relation to the pusher 20 after disengagement. In FIGS. 2A-2E, the distal portion 24 of the pusher 20 and the proximal portion 29 of the lancet holder 25 are illustrated as having the shape of a half-cylinder. Other shapes or cross-sections are also contemplated, e.g. one or more recesses adapted to accommodate one or more corresponding protruding portions.

Turning now to FIGS. 3A-3D, another embodiment of the activation/retraction mechanism is here illustrated. Again, the housing, the locking member, and the biasing members acting on the components have been omitted so as not to clutter the drawings. In this embodiment, the pusher 30 is provided with a flexible pusher arm 31 extending in a distal direction towards the lancet holder 35. A distal end 33 of the at least one pusher arm 31 comprises an engagement surface 32 arranged to engage the proximal end 38 of the lancet holder 35 and a camming surface 34. The camming surface 34 is arranged to come into contact with an abutment 36 in the housing arranged in a position corresponding to the predetermined length from the initial position of the pusher 30, and adapted to deflect the at least one pusher arm 31 laterally to disengage the at least one pusher arm 31 from the proximal end 38 of the lancet holder 35 when the pusher 30 is urged against the abutment 36 in the distal direction.

Figure 3A:
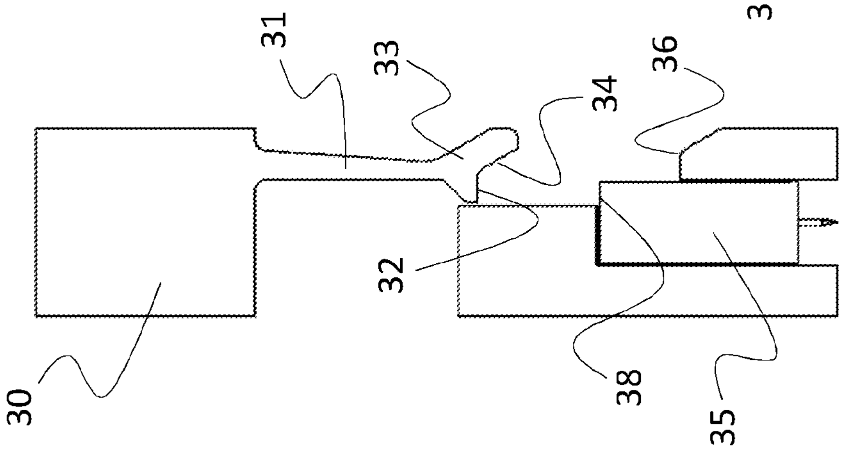
FIGS. 3A-3D show views of an activation/retraction mechanism according to a third embodiment of the present invention in different stages of operation.

FIG. 3A shows the activation/retraction mechanism in an initial stage (before firing) wherein the pusher 30 is retained in a proximal position, and the lancet holder 35 is biased towards its proximal position with the lancet not protruding from the housing.

Figure 3B:
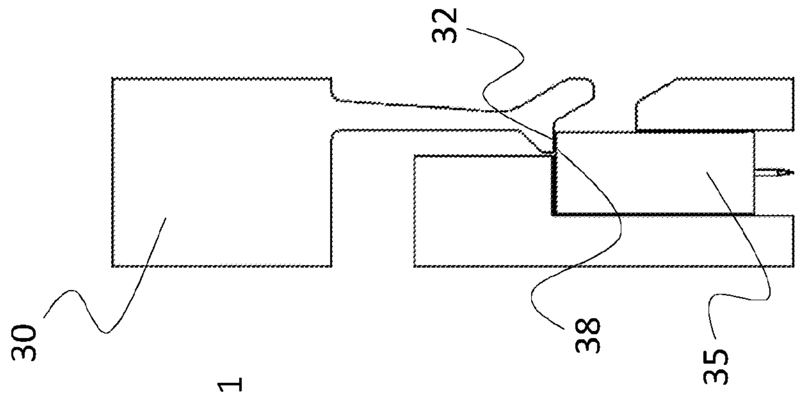

FIG. 3B shows the activation/retraction mechanism shortly after firing, the pusher 30 has been released and displaced distally by the first biasing member so that the engagement surface 32 on the distal end 33 of the pusher arm 31 abuts against the proximal end 38 of the lancet holder 35. Further displacement of the pusher 30 in the distal direction will also displace the lancet holder 35. The engagement surface 32 is preferably planar and faces towards the lancet holder 35 in the distal direction.

Figure 3C:
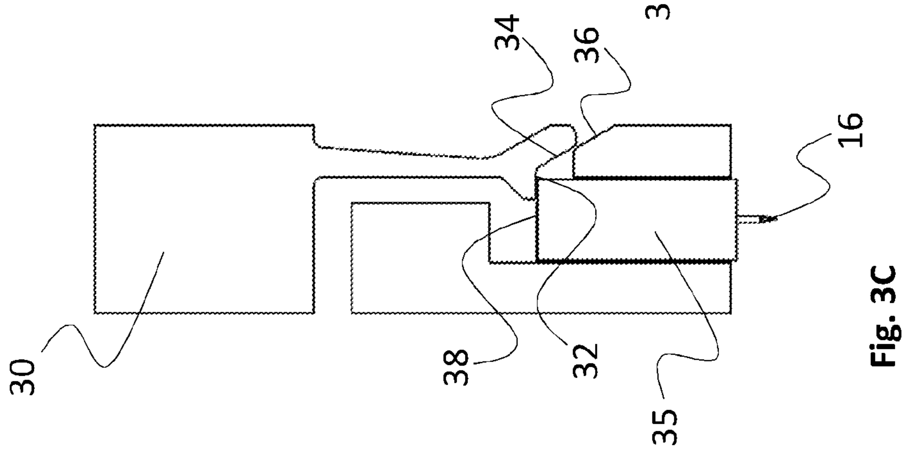

FIG. 3C shows the activation/retraction mechanism in a further advanced stage, wherein the pusher 30 and the lancet holder 35 both have been displaced further in the distal direction owing to the abutment 36 between the engagement surface 32 on the distal end 33 of the pusher arm 31 and the proximal end 38 of the lancet holder 35. In this position, the camming surface 34 on the distal end 33 of the pusher arm 31 is brought into contact with the abutment 36 in the housing. As may be seen, the abutment 36 may also comprise a corresponding camming surface 34. Further displacement of the pusher 30 in the distal direction will urge the camming surface 34 on the distal end 33 of the pusher arm 31 against the abutment 36 and cause it to be deflected laterally, i.e. away from the lancet holder 35, until the pusher arm 31 is disengaged from the lancet holder 35.

Figure 3D:
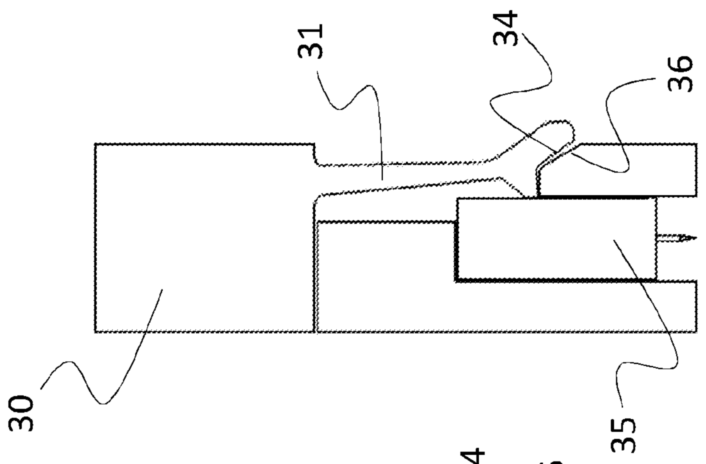

FIG. 3D shows the activation/retraction mechanism in a final stage at the end of the firing stroke. After the disengagement from the pusher arm 31, the lancet holder 35 is allowed to be displaced by the second biasing member in a proximal direction towards its initial, retracted position, wherein the lancet 16 does not protrude from the housing.

Turning now to FIG. 4 and FIGS. 5A-5F, an alternative embodiment of the activation/retraction mechanism working under a similar principle to the one shown in FIGS. 3A-3D is illustrated. The activation/retraction mechanism comprises a pusher 40 adapted to be displaced distally by means of a first biasing member 66 and a lancet holder 45 comprising a lancet 16 and adapted to be engaged and displaced distally by the pusher 40. Further, the lancet holder 45 is arranged to be displaced in a proximal direction by a second biasing member 47. The pusher 40 including the first biasing member 66, and the lancet holder 45 including the lancet 16 and the second biasing member 47 are arranged in a housing 65. FIG. 4 and FIGS. 5A-5F show the internal space of the housing 65 in a cutaway view and the components arranged therein.

In this embodiment, the pusher 40 comprises two oppositely arranged, flexible pusher arms 41 extending distally, each comprising an engagement surface 42 and a camming surface 44 on a distal end 43 thereof. Similar to the embodiment of FIGS. 3A-3D, the housing 65 comprises corresponding abutments 46, with which the camming surfaces 44 are arranged to be brought into contact. Furthermore, the activation/retraction mechanism as illustrated in FIG. 4 comprises additional safety features to prevent accidental firing of the lancing device and protect against injury from the sharp point of the lancet 16.

Firstly, a lancet or needle guard is provided at the distal end 43. The lancet guard 67 may be integrally formed with a distal end 49 of the lancet holder 45 by means of a frangible portion adapted to break when the lancet guard 67 is displaced in relation to the lancet 16. For instance, the lancet guard 67 is adapted to break off from the lancet holder 45 by twisting or pulling the lancet guard 67 away. Additionally, the lancet holder 45 may comprise lateral projections 62 which cooperate with corresponding recesses 64 in the housing 65 which allow rotation of the lancet holder 45 within a predetermined angular range. Hence, when the lancet guard 67 is twisted, the lancet holder 45 will be rotated until the lateral projections 62 abut against end surfaces of the recesses 64 in the housing 65 to prevent further rotation. When the operator twists the lancet guard 67 further, the applied torque will break the frangible portions such that the lancet guard 67 may be removed, and the activation/retraction mechanism will be ready for use.

Figure 4:
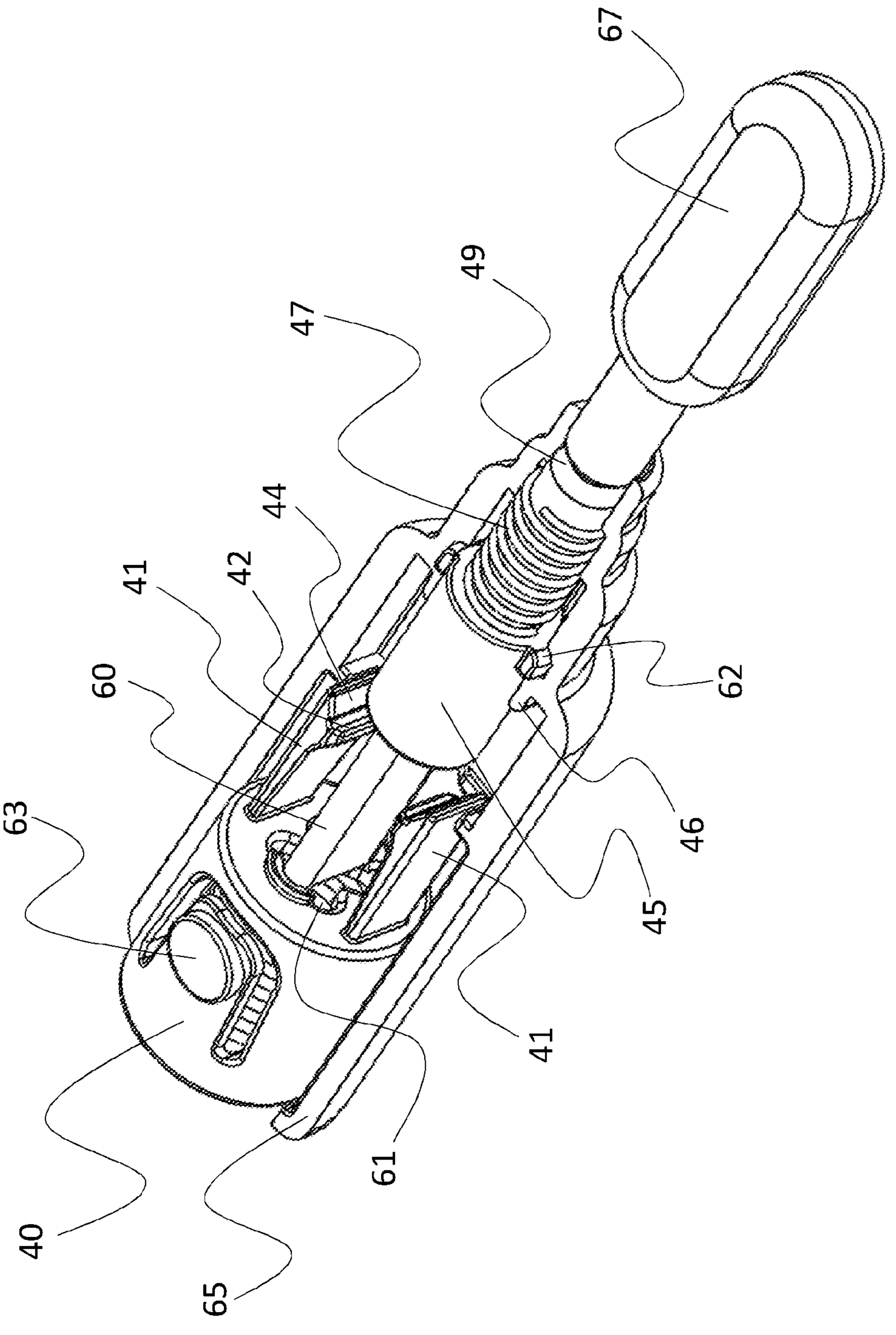
FIG. 4 shows a perspective view of an alternative activation/retraction mechanism according to a third embodiment of the present invention.

FIG. 4 also shows a second safety feature of the activation/retraction mechanism which prevents accidental firing of the lancing device. To that end, the lancet holder 45 comprises a guide rod 60 rigidly connected to, or integrally formed with, a proximal end 48 of the lancet holder 45 and extending proximally towards the pusher 40. The cross-section of the guide rod 60 preferably exhibits rotational symmetry of order 2 with respect to its longitudinal axis, i.e. the shape of the guide rod 60 is the same when rotated 180° but varies in the range 0-180°. One such example is given in FIG. 4, wherein the guide rod 60 is shaped like a flat bar.

The pusher 40 in this embodiment is hollow and the first biasing member 66 is arranged in an internal space of the pusher 40. The pusher 40 also comprises a through-going hole 61 adapted to the cross-sectional shape of the guide rod 60. However, in an initial position of the guide rod 60, the hole 61 in the pusher 40 is arranged misaligned with respect to the guide rod 60 such that distal movement of the pusher 40 is prevented. Rotation of the lancet holder 45 a predetermined angle, for instance 45°, in relation to the pusher 40 brings the guide rod 60 into alignment with the hole 61, which allows the guide rod 60 to enter through the hole 61 and the pusher 40 to be displaced distally along the guide rod 60.

It is understood that the features of the safety assembly (lancet guard, guide rod and hole) may be employed in a lancing device independently of the activation/retraction mechanism of the present invention.

Similar to the locking member described in relation to FIGS. 1A-1D, the activation/retraction mechanism comprises a depressible button 63 arranged on a flexible flap which is formed by a recess in the pusher 40. In an initial stage, the button 63 is seated in a hole 61 (not shown) in the housing 65 65. Depressing the button 63 releases the pusher 40 from the housing 65 to initiate the firing stroke.

Figure 5C:
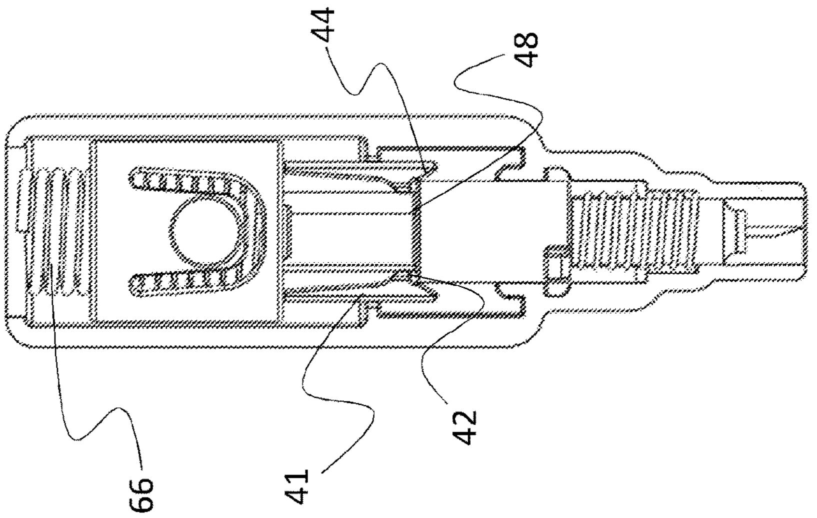
FIGS. 5A-5F show views of an activation/retraction mechanism according to FIG. 4 in different stages of operation.
Figure 5B:
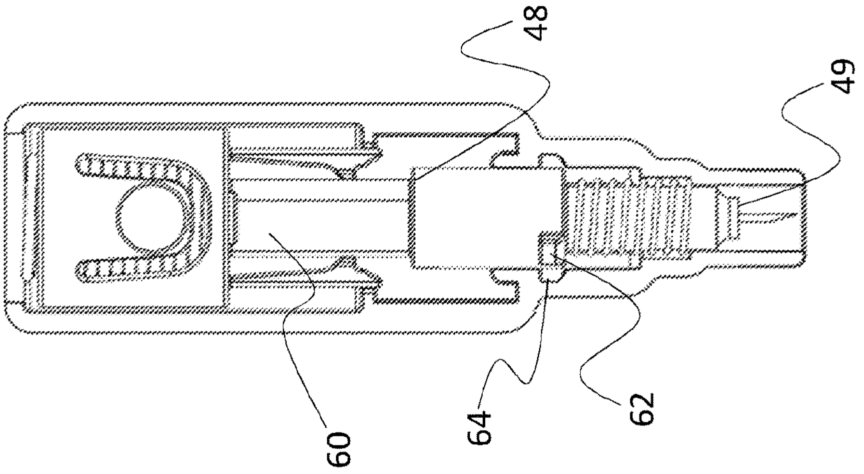
Figure 5A:
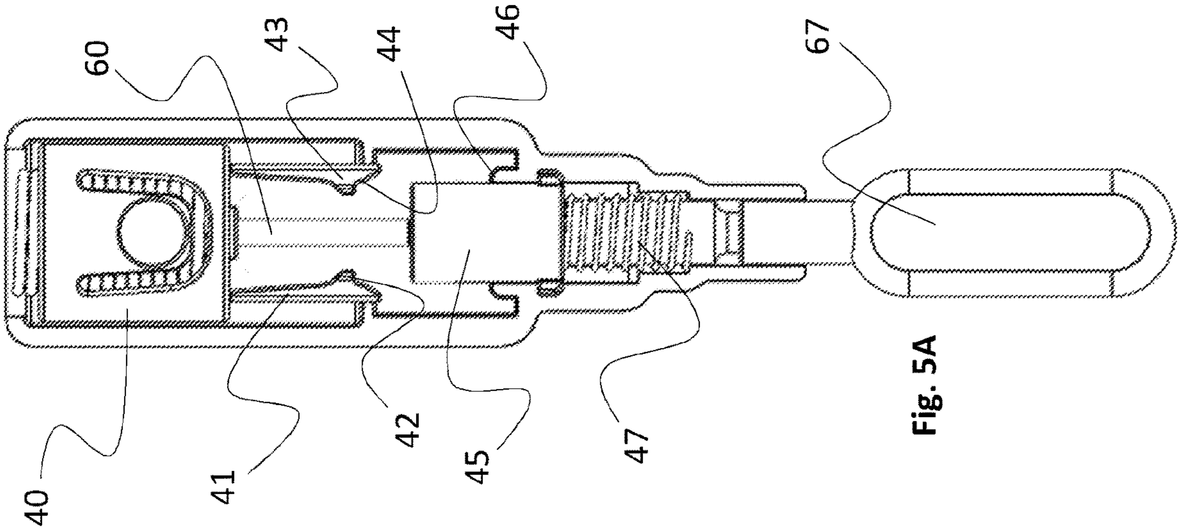

FIG. 5A shows the activation/retraction mechanism of FIG. 4 in an initial stage (before firing) wherein the pusher 40 is retained in a proximal position, and the lancet holder 45 is biased towards its proximal position. Also, the lancet guard 67 is in place covering the distal sharp point of the lancet 16.

FIG. 5B shows the activation/retraction mechanism of FIG. 4 in a ready state, wherein the lancet guard 67 has been removed by twisting it off, which causes the lancet holder 45 and guide rod 60 to be rotated about a predetermined angle until the lateral projections 62 have reached and abut against the end surfaces of the corresponding recesses 64 (not shown) in the housing 65. The rotation brings the guide rod 60 into alignment with the hole 61 in the pusher 40 to allow the pusher 40 to be displaced distally through a sliding motion on the guide rod 60.

FIG. 5C shows the activation/retraction mechanism shortly after firing, the pusher 40 has been released and displaced distally by the first biasing member 66 so that the engagement surfaces 42 on the distal end 43 of each pusher arm 41 abut against the proximal end 48 of the lancet holder 45. Further displacement of the pusher 40 in the distal direction will also displace the lancet holder 45. The engagement surfaces 42 are preferably planar and face towards the lancet holder 45 in the distal direction.

Figure 5F:
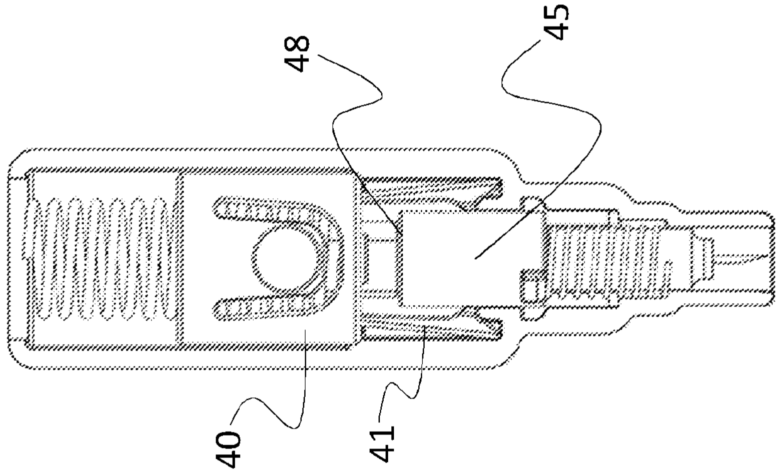
Figure 5E:
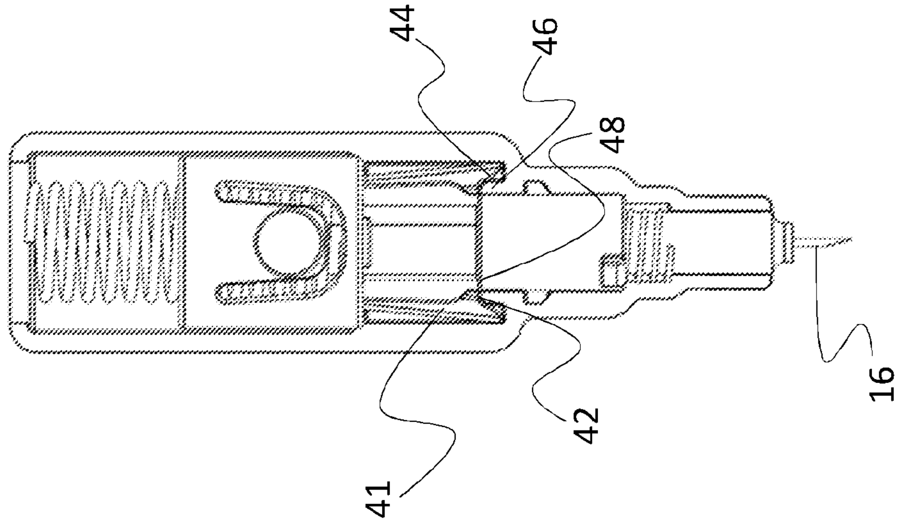
Figure 5D:
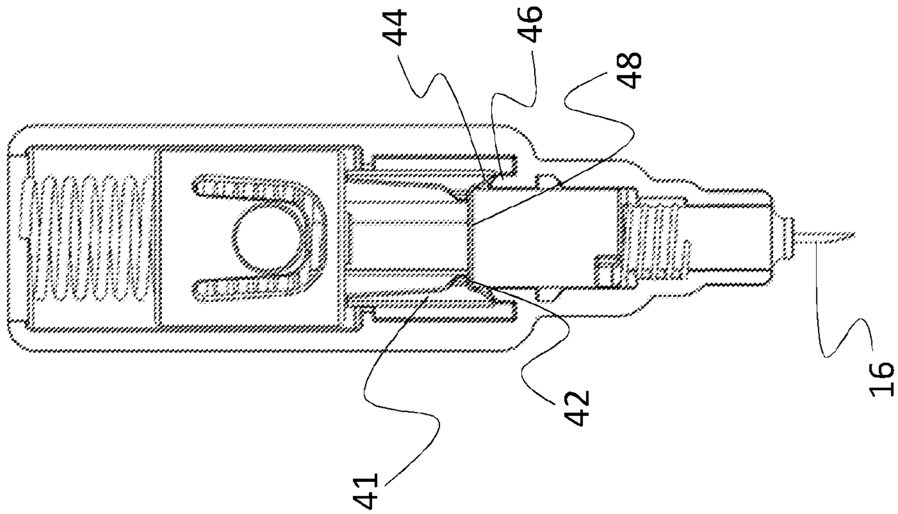

FIG. 5D shows the activation/retraction mechanism in a further advanced stage, wherein the pusher 40 and the lancet holder 45 both have been displaced further in the distal direction owing to the abutment between the engagement surfaces 42 on the distal end 43 of each pusher arm 41 and the proximal end 48 of the lancet holder 45. The lancet 16 now protrudes out of the housing 65 to penetrate the skin of the subject. In this position, the camming surfaces 44 on the distal end 43 of each pusher arm 41 are brought into contact with the corresponding abutments 46 in the housing 65.

FIG. 5E shows the activation/retraction mechanism at or near the end of the firing stroke. Further displacement of the pusher 40 in the distal direction has urged the camming surfaces 44 on the distal end 43 of each pusher arm 41 against the abutments 46 and caused them to deflect laterally, i.e. away from the lancet holder 45, such that the pusher arms 41 are disengaged from the lancet holder 45.

FIG. 5F shows the activation/retraction mechanism in a final stage at the end of the firing stroke. After the disengagement from the pusher arms 41, the lancet holder 45 is free to be displaced by the second biasing member 47 in a proximal direction towards its initial, retracted position, wherein the lancet 16 does not protrude from the housing 65. The first biasing member 66 continues to bias the pusher 40 distally, thus maintaining the pusher 40 in the distal position with the pusher arms 41 laterally deflected.

Turning now to FIGS. 6A-6D, a further alternative embodiment of the activation/retraction mechanism is here illustrated. In this embodiment, the first biasing member acts as the pusher. The first biasing member comprises a spiral wound torsion spring arranged in a proximal end of the housing with its axis of rotation substantially perpendicular to the longitudinal extension of the housing. A free end of the torsion spring which extends a predetermined length from the axis of rotation is arranged to act as the pusher, wherein rotation of the torsion spring causes the free end to engage the proximal end of the lancet holder and displace the lancet holder distally. Furthermore, the housing comprises a recess in the wall thereof arranged to receive the free end of the torsion spring when the free end reaches its distalmost position. The recess is dimensioned and positioned such that the free end is moved sufficiently in a lateral direction to be disengaged from the proximal end of the lancet holder. The lancet holder is thereby free to return to its initial, retracted position under influence of the second biasing member.

Figure 6D:
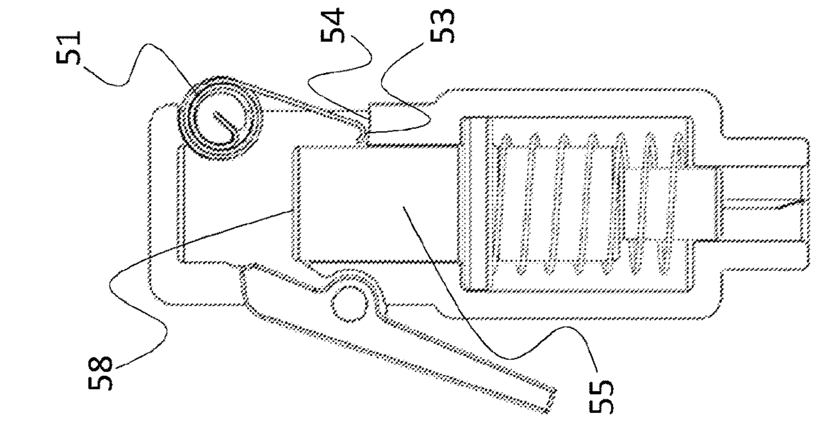
FIGS. 6A-6D show views of an activation/retraction mechanism according to a third embodiment of the present invention in different stages of operation.
Figure 6C:
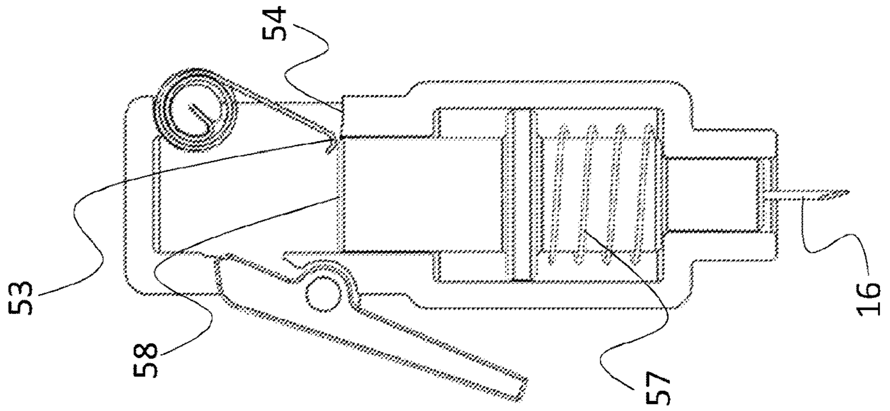
Figure 6B:
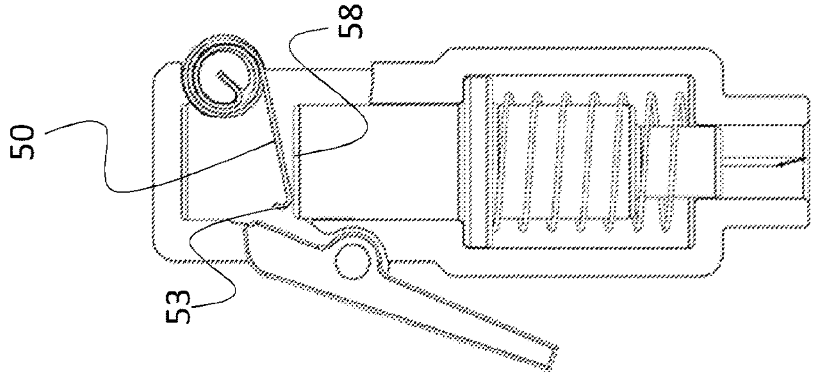
Figure 6A:
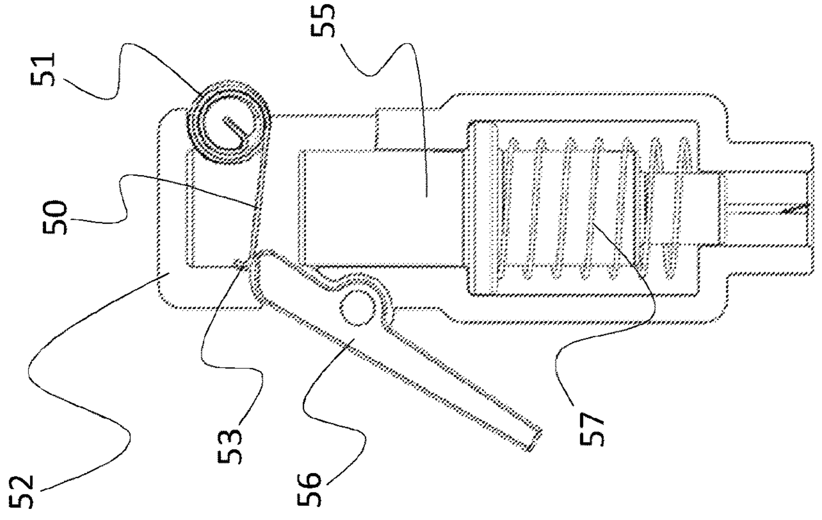

FIG. 6A shows the activation/retraction mechanism in an initial stage (before firing) wherein the free end of the torsion spring is retained in a proximal position by a releasable locking member. The first biasing member is here in a prestressed state, wound in a clockwise direction, and oriented substantially perpendicular to the longitudinal extension of the housing (i.e. in the 9 o'clock position). The locking member is here shown as a lever with a catch engaging the free end of the torsion spring and is arranged to pivot about an axis to release the free end. Other variants of the locking member are also envisaged.

In FIG. 6B, the locking member has been actuated and the free end of the torsion spring has been released to rotate about the axis of rotation of the torsion spring in an anticlockwise direction due to unwinding of the torsion spring. The anti-clockwise rotation also causes the free end to be displaced in a distal direction. After travelling a short distance, the free end of the torsion spring reaches and abuts against the proximal end of the lancet holder. Further displacement of the free end of the torsion spring thus also displaces the lancet holder in a distal direction.

In FIG. 6C, at or near the end of the firing stroke, the free end of the torsion spring has been rotated towards its distalmost position, approximately between the 6 and 7 o'clock position. The lancet holder has also reached its distalmost position wherein the lancet extends out of the distal opening of the housing to penetrate the skin, and the second biasing member has been compressed. During rotation, the free end of the torsion spring slides laterally along the surface of the proximal end of the lancet holder such that the contact point between them gradually shifts from left to right, as illustrated in FIGS. 6B and 6C.

FIG. 6D shows the activation/retraction mechanism in a final stage, wherein the free end of the torsion spring has been rotated further to be received in the recess arranged in the wall of the housing. When the free end of the torsion spring enters the recess, it loses contact with the proximal end of the lancet holder, and as a result, the proximal end of the lancet holder is disengaged from the free end of the torsion spring. The lancet holder is then free to be displaced by the second biasing member in a proximal direction towards its initial, retracted position, wherein the lancet does not protrude from the housing.

The first biasing member and/or the second biasing member preferably comprise a resilient spring, such as a helical coil spring. However, other means for biasing are also contemplated, such as for instance a flat coil spring or a spring steel plate.

Preferred embodiments of an activation/retraction mechanism for a lancing device according to the invention have been described. However, the person skilled in the art realises that this can be varied within the scope of the appended claims without departing from the inventive idea.

All the described alternative embodiments above or parts of an embodiment can be freely combined or employed separately from each other without departing from the inventive idea as long as the combination is not contradictory.

The invention claimed is:

1. An activation/retraction mechanism for a lancing device comprising: a pusher arranged in a housing of the lancing device and configured for translational movement within the housing; a first biasing member arranged to displace the pusher distally within the housing; a lancet holder arranged in the housing and comprising a lancet for penetrating skin of a subject; and a second biasing member arranged to displace the lancet holder proximally within the housing; wherein the lancet holder and the pusher are arranged in the housing in such a way that a distal end of the pusher engages a proximal end of the lancet holder to push the lancet holder from an initial position in a distal direction when the first biasing member displaces the pusher distally, wherein the distal end of the pusher and the proximal end of the lancet holder are arranged to disengage from each other when the pusher has been displaced distally a predetermined length from its initial position, wherein the first biasing member is arranged to maintain the pusher in a distal position after disengagement from the lancet holder, wherein the second biasing member is configured to cause movement of the lancet holder toward the initial position after disengagement from the pusher, wherein the activation/retraction mechanism is configured so that, after disengagement of the pusher from the lancet holder, the pusher is in the distal position, in which the distal end of the pusher is positioned distally of the proximal end of the lancet holder, and wherein an engagement surface of the proximal end of the lancet holder is perpendicular to a displacement direction of the lancet holder.

2. The activation/retraction mechanism according to claim 1, wherein a distal portion of the pusher and a proximal portion of the lancet holder have complementary cross-sections and have a combined cross-sectional area smaller than a cross-sectional area of the housing such that the distal portion of the pusher and the proximal portion of the lancet holder are free to move in relation to each other when the distal end of the pusher is disengaged from the proximal end of the lancet holder.

3. The activation/retraction mechanism according to claim 2, wherein the pusher and the lancet holder are arranged at a non-zero angle to each other such that the distal end of the pusher moves laterally in relation to the proximal end of the lancet holder when the first biasing member displaces the pusher distally until they disengage from each other.

4. The activation/retraction mechanism according to claim 2, wherein the pusher comprises an external helical groove or ridge arranged to cooperate with a guide projection arranged in the housing to rotate the pusher when the first biasing member displaces the pusher distally, such that the distal end of the pusher rotates in relation to the proximal end of the lancet holder until they disengage from each other.

5. The activation/retraction mechanism according to claim 1, wherein the pusher comprises at least one pusher arm extending in the distal direction, wherein a distal end of the at least one pusher arm comprises an engagement surface arranged to engage the proximal end of the lancet holder and a camming surface, wherein the camming surface is arranged to come into contact with an abutment in the housing arranged in a position corresponding to the predetermined length from the initial position of the pusher and adapted to deflect the at least one pusher arm laterally to disengage the at least one pusher arm from the proximal end of the lancet holder when the pusher is urged against the abutment in the distal direction.

6. The activation/retraction mechanism according to claim 5, wherein the pusher comprises two pusher arms.

7. The activation/retraction mechanism according to claim 5, further comprising a safety assembly comprising a lancet guard integrally formed with a distal end of the lancet holder by means of a frangible portion adapted to break when the lancet guard is displaced in relation to the lancet holder.

8. The activation/retraction mechanism according to claim 7, wherein the lancet holder further comprises one or more projections arranged to cooperate with corresponding recesses in the housing which allow rotation of the lancet holder within a predetermined angular range.

9. The activation/retraction mechanism according to claim 7, wherein the safety assembly further comprises a guide rod rigidly connected to or integrally formed with the proximal end of the lancet holder, wherein the pusher comprises a through-going hole adapted to the shape of the guide rod such that rotation of the lancet holder a predetermined angle in relation to the pusher brings the guide rod into alignment with the hole to allow the pusher to be displaced distally along the guide rod.

10. The activation/retraction mechanism according to claim 1, wherein the first biasing member and/or second biasing member comprises a spring.

11. The activation/retraction mechanism according to claim 1, further comprising a releasable locking member arranged to retain the pusher and the first biasing member in a prestressed state.

12. The activation/retraction mechanism according to claim 1, wherein the pusher is arranged at a distance from the lancet holder in an initial stage such that the distal end of the pusher is separated from the proximal end of the lancet holder.

13. The activation/retraction mechanism according to claim 1, wherein the pusher is configured to remain in contact with the lancet holder from contact with the lancet holder until the disengagement between the distal end of the pusher and the proximal end of the lancet holder.

14. The activation/retraction mechanism according to claim 1, wherein the first biasing member is configured to resiliently deform to permit distal movement of the pusher.

15. The activation/retraction mechanism according to claim 1, wherein the pusher is configured for translational movement within the housing along a longitudinal axis of the housing.

16. The activation/retraction mechanism according to claim 15, wherein the pusher is configured for translational movement within the housing parallel to the longitudinal axis of the housing.

17. The activation/retraction mechanism according to claim 1, wherein the pusher and the lancet are configured so that axial movement of the pusher in the distal direction to a position distal of the initial position of the pusher by the predetermined length causes disengagement of the distal end of the pusher from the proximal end of the lancet.

18. A lancing device comprising an activation/retraction mechanism, the activation/retraction mechanism comprising:

a pusher;

a first biasing member arranged to displace the pusher linearly in a distal direction;

a lancet holder comprising a lancet for penetrating skin of a subject; and a second biasing member arranged to displace the lancet holder in a proximal direction from an initial position;

wherein the lancet holder and the pusher are arranged in a housing of the lancing device in such a way that a distal end of the pusher engages a proximal end of the lancet holder to push the lancet holder in a distal direction when the first biasing member displaces the pusher distally, wherein the distal end of the pusher and the proximal end of the lancet holder are arranged to disengage from each other when the pusher has been displaced distally a predetermined length from its initial position, wherein the first biasing member is arranged to maintain the pusher in a distal position after disengagement from the lancet holder, wherein the second biasing member is configured to cause movement of the lancet holder toward the initial position after disengagement from the pusher, wherein the activation/retraction mechanism is configured so that, after disengagement of the pusher from the lancet holder, the pusher is in the distal position, in which the distal end of the pusher is positioned distally of the proximal end of the lancet holder, and wherein an engagement surface of the proximal end of the lancet holder is perpendicular to a displacement direction of the lancet holder.

* * * * *